United States Patent [19]
Eyre

[11] Patent Number: 5,912,131
[45] Date of Patent: *Jun. 15, 1999

[54] DETECTION OF TYPE 1 COLLAGEN DEGRADATION IN VIVO

[75] Inventor: David R. Eyre, Mercer Island, Wash.

[73] Assignee: Washington Research Foundation, Seattle, Wash.

[*] Notice: This patent is subject to a terminal disclaimer.

[21] Appl. No.: 08/965,699

[22] Filed: Nov. 7, 1997

Related U.S. Application Data

[63] Continuation of application No. 08/561,842, Nov. 22, 1995, Pat. No. 5,688,652, which is a continuation of application No. 08/229,569, Apr. 19, 1994, Pat. No. 5,472,884, which is a continuation of application No. 07/708,529, May 31, 1991, Pat. No. 5,320,970, which is a continuation-in-part of application No. 07/614,719, Nov. 21, 1990, Pat. No. 5,300,434, which is a continuation-in-part of application No. 07/444,881, Dec. 1, 1989, Pat. No. 5,140,103, which is a continuation-in-part of application No. 07/118,234, Nov. 6, 1987, Pat. No. 4,973,666.

[51] Int. Cl.$^6$ ............................................. G01N 33/53
[52] U.S. Cl. ..................... 435/7.1; 436/501; 436/518; 436/536; 436/541; 530/387.1; 530/388.1; 530/389.1
[58] Field of Search ................... 435/7.1; 436/501, 436/518, 536, 541; 530/387.1, 388.1, 389.1

[56] References Cited

U.S. PATENT DOCUMENTS

| | | |
|---|---|---|
| 3,600,132 | 8/1971 | Goverde . |
| 4,094,646 | 6/1978 | Stern et al. . |
| 4,298,593 | 11/1981 | Ling . |
| 4,312,853 | 1/1982 | Timpl . |
| 4,371,374 | 2/1983 | Cerami et al. . |
| 4,504,587 | 3/1985 | Timpl et al. . |
| 4,628,027 | 12/1986 | Gay ............................................. 435/7 |
| 4,731,326 | 3/1988 | Thompson et al. . |
| 4,774,227 | 9/1988 | Piez et al. . |
| 4,973,666 | 11/1990 | Eyre . |
| 5,140,103 | 8/1992 | Eyre . |
| 5,300,434 | 4/1994 | Eyre . |
| 5,320,970 | 6/1994 | Eyre . |
| 5,455,179 | 10/1995 | Eyre . |
| 5,472,884 | 12/1995 | Eyre . |
| 5,473,052 | 12/1995 | Eyre . |
| 5,532,169 | 7/1996 | Eyre . |
| 5,576,189 | 11/1996 | Eyre . |
| 5,607,862 | 3/1997 | Eyre . |

FOREIGN PATENT DOCUMENTS

| | | |
|---|---|---|
| 128 041 | 6/1983 | European Pat. Off. . |
| 289 314 | 4/1988 | European Pat. Off. . |
| 0 505 210 A2 | 9/1992 | European Pat. Off. . |
| 0 4234 428 B1 | 9/1994 | European Pat. Off. . |
| 394 296 | 1/1995 | European Pat. Off. . |
| 502 928 | 1/1996 | European Pat. Off. . |
| 2205643 | 5/1987 | United Kingdom . |
| WO 88/08980 | 11/1988 | WIPO . |
| WO 89/04491 | 5/1989 | WIPO . |
| WO 89/12824 | 12/1989 | WIPO . |
| WO 90/04417 | 5/1990 | WIPO . |
| WO 90/08195 | 7/1990 | WIPO . |
| WO 91/08478 | 6/1991 | WIPO . |
| WO 92/21698 | 12/1992 | WIPO . |

OTHER PUBLICATIONS

Black, et al., "Urinary excretion of the hydroxypyridinium cross links of collagen in patients with rheumatoid arthritis," *Annals of the Rheumatic Diseases,* 48:641–644 (1989).

Seibel, et al., "Urinary Hydroxy–pyridinium Crosslinks Provide Indices of Cartilage and Bone Involvement in Arthritic Diseases," the *Journal of Rheumatology,* 16:964–970 (1989).

Baldwin, et al., "Structure of cDNA clones coding for human type II procollagen: the a1(II) chain is more similar to the a1(I) chain than two other a chains of fibrillar collagens," *Biochemistry Journal,* 262:521–528 (1989).

Ala–Kokko, et al., "Structure of cDNA clones coding for the entire preproal(III) chain of human type III procollagen: Differences in protein structure from type I procollagen and conservation of codon preferences," *Biochemistry Journal,* 260:509–516 (1989).

Seibel, "Komponenten der extrazllularen Gewebematrix als potentielle 'Marker' des Bindegewebs–, Knorpel– und Knochenmetabolismus bei Erkrankungen des Bewegungsapparates," *Zeitschrift fur Rheumatologie,* 48:6–18 (1989).

Dodge and Poole, "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1," Journal of Clinical Investigation, 83:647–661 (1989).

Niemela, "Radioimmunoassays for Type III Procollagen Amino–Terminal Peptides In Humans," *Clinical Chemistry,* 31:1301–1304 (1985).

Sangiorgi, et al., "Isolation and partial characterization of the entire human proal(II) collagen gene," *Nucleic Acids Research,* 13:2207–2225 (1985).

Loidl, et al., "Molecular cloning and carboxyl–propeptide analysis of human type III procollagen," *Nucleic Acids Research,* 12:9383–9394 (1984).

Wu and Eyre, "Identification of Hydroxypyridinium Cross–Linking Sites in Type II Collagen of Bovine Articular Cartilage," *Biochemistry,* 23:1850–1857 (1984).

Pierard, et al., "Radioimmunoassay for the Amino–Terminal Sequences of Type III Procollagen in Human Body Fluids Measuring Fragmented Precursor Sequences," *Analytical Biochemistry,* 141:127–136 (1984).

(List continued on next page.)

Primary Examiner—Jeffrey Stucker
Attorney, Agent, or Firm—Christenson O'Connor Johnson & Kindness PLLC

[57] ABSTRACT

Compositions useful in quantitating collagen peptides to determine the rate of bone resorption are prepared by treating bone with a protease, such as collagenase, and purifying the compositions so as to enrich them with peptides that contain 3-hydroxypyridinium cross-links.

4 Claims, 1 Drawing Sheet

OTHER PUBLICATIONS

Rohde, et al., "Radioimmunoassay for type III procollagen peptide and its application to human liver disease," *European Journal of Clinical Investigation,* 9:451–459 (1979).

Russell, R.G.G., et al., "Biochemical Markers of Bone Turnover in Paget's Disease," *Metab. Bone Dis. & Rel. Res.,* 4 & 5:255–262 (1981).

Drinkwater, B.L., et al., "Bone Mineral Density After Resumption of Menses in Amenorrheic Athletes," *JAMA,* 256:380–382 (1986).

Drinkwater, B.L., et al., "Bone Mineral Content of Amenorrheic and Eumenorrheic Athletes," the *New England Journal of Medicine,* 311:5;277–281 (1984).

Fujimoto, D., "Evidence for Natural Existence of Pyridinoline Crosslink in Collagen," *Biochemical and Biophysical Research Communications,* 93:948–953 (1980).

Yamauchi, M. et al., "A Comparative Study of the Distribution of the Stable Crosslink, Pyridinoline, in Bone Collagens from Normal, Osteoblastoma, and Vitamin D–Deficient Chicks," *Biochemical and Biophysical Research Communications,* 102:59–65 (1981).

Kuboki, Y., et al., "Location of the Intermolecular Crosslinks in Bovine Dentin Collagen, Solubilization with Trypsin and Isolation of Cross–Link Peptides Containing Dihydroxylysinonorleucine and Pyridinoline," *Biochemical and Biophysical Research Communications,* 102:119–126 (1981).

Gunja–Smith, Z. and Boucek, R.J., "Collagen cross–linking compounds in human urine," *Biochemical Journal,* 197:759–762 (1981).

Tsuchikura, O., et al., "Pyridinoline Fluorescence in Cyanogen Bromide Peptides of Collagen," *Biochemical and Biophysical Research Communications,* 102:1203–1208 (1981).

Tsuda, M., et al., "Pyridinoline is a Real Moiety of Collagen," *Biochemical and Biophysical Research Communications,* 104:1407–1412 (1982).

Robins, S.P., "An enzyme–linked immunoassay for the collagen cross–link pyridinoline," *Biochemical Journal,* 207:617–620 (1982).

Banes, A.J., et al., "Nonmineralized and Mineralized Compartments of Bone: the Role of Pyridinoline in Nonmineralized Collagen," *Biochemical and Biophysical Research Communications,* 113:975–981 (1983).

Fujimoto, D., et al., "Analysis of Pyridinoline, a Cross–Linking Compound of Collagen Fibers, in Human Urine," *J. Biochem.,* 94:1133–1136 (1983).

Eyre, D.R., et al., "Cross–Linking in Collagen and Elastin," *Ann. Rev. Biochem.,* 53:717–748 (1984).

Light, N. and Bailey, A.J., "Collagen crosslinks: Location of pyridinoline in type I collagen," *FEBS* 2409, 182:503–508 (1985).

Wu, J–J. and Eyre, D.R., "Fine Powdering Exposes the Mineral–Protected Collagen of Bone to Protease Digestion," *Calcif. Tissue Int.,* 42:243–247 (1988).

Fujimoto, D., et al., "Pyridinoline, A Non–Reducible Crosslink of Collagen. Quantitative Determination, Distribution, and Isolation of a Crosslinked Peptide," *Chemical Abstracts* 89(11):148, (Sep. 11, 1978).

Black, D., et al., "Quantitative Analysis of the Pyridinium Crosslinks of Collagen in Urine Using Ion–Paired Reversed– Phase High–Performance Liquid Chromatography," *Chemical Abstracts* 108(21):354, (May 23, 1988).

Fujimoto, D., et al., "Analysis of Pyridinoline, A Cross–Linking Compound of Collagen Fibers, in Human Urine," *Chemical Abstracts* 99(19):446–447, (Nov. 7, 1983).

Macek, J., et al., "Determination of Collagen Degradation Products in Human Urine in Osteoarthrosis," *Chemical Abstracts* 108(3):299, (Jan. 18, 1988).

Eyre, D.R., et al., "Quantitation of Hydroxypyridinium Crosslinks in Collagen by High–Performance Liquid Chromatography," *Analytical Biochemistry,* 137:380–388 (1984).

Robins, S.R., et al., "Measurement of the cross linking compound, pyridinoline, in urine as an index of collagen degradation in joint disease," *Annals of the Rheumatic Diseases,* 45:969–973 (1986).

Bernard, M.P., et al., "Nucleotide Sequences of Complementary Deoxyribonucleic Acids for the Proal Chain of Human Type I Procollagen. Statistical Evaluation of Structures that are Conserved During Evolution," *Biochemistry,* 22:5213–5223 (1983).

Goldstein, D., et al., "Simultaneous Measurement of DOPA, DOPAC, and Catecholamines in Plasma by Liquid Chromatography with Electrochemical Detection," *ESA Review,* vol. II, No. 1, 2–11 (1986).

Chu, M–L., et al., "Human proal(I) collagen gene structure reveals evolutionary conservation of a pattern of introns and exons," *Nature* 310(26):337–340 (1984).

Robins, S.P., et al., "Measurement of Hydroxypyridinium Crosslinks of Collagen as an Index of Bone Matrix Degradation," *An Abstract of a Paper,* Lake Garda, Italy (1987).

Kang, A.H. and Gross, J., "Amino Acid Sequence of Cyanogen Bromide Peptides from the Amino–Terminal Region of Chick Skin Collagen," *Biochemistry* 9:796–804 (1970).

Highberger, J.H., et al., "The Amino Acid Sequence of Chick Skin Collagen a1–CB7," *Biochemistry* 14(13):2872–2881 (1975).

Fietzek, P.P. and Kuhn, K., "The Covalent Structure of Collagen: Amino Acid Sequence of the N–Terminal Region of a2–CB5 from Rat Skin Collagen," *FEBS Letters* 36(3):289–291 (1973).

Dixit, S.N., et al., "Covalent Structure of Collagen: Amino Acid Sequence of a2–CB5 of Chick Skin Collagen Containing the Animal Collagenase Cleavage Site," *Biochemistry,* 18:3416–3422 (1979).

Dakkak, et al., "Modifications de l'hydroxyprolinurie peptidique au cours de la maladie de Paget et des ostéomes," *Ann. Biol. Clin.* 37:195–200 (1979).

Teitsson, et al., "Urinary excretion of pyridinium metabolites in a patient with Paget's Disease: new markers for collagen break–down," Abstracts, Scottish Society of Experimental Medicine, May 13, 1988.

Eyre, et al., "Collagen cross–linking in human bone and articular cartilage: Age–related changes in the content of mature hydroxypyridinium residues," *Biochem. J.* 252:495–500 (1988).

Whittle, et al., "Biochemical investigation of possible lesions in human aorta that predispose to dissecting aneurysms: pyridinoline crosslinks," *Cardiovascular Research* 21:161–168 (1987).

Gunja–Smith, Z., "An Enzyme–Linked Immunosorbent Assay to Quantitate the Elastin Crosslink Desmosine in Tissue and Urine Samples," *Analytical Biochemistry* 147:258–264 (1985).

Schuppan, et al., "Radioimmunoassay for the Carboxy-terminal Cross-linking Domain of Type IV (Basement Membrane) Procollagen in Body Fluids," *J. Clin. Invest.* 78:241–248 (Jul. 1986).

Eyre, D., "Collagen Cross–Linking Amino Acids," In: *Methods in Enzymology*, vol. 144, pp. 115–139, Academic Press, Inc., 1987.

Eyre, et al., "Identification of urinary peptides derived from cross–linking sites in bone collagen in Paget's Disease," *Journal of Bone and Mineral Research*, 3, Supp. 1 (Jun. 1988).

Eyre, et al., "Reducible Crosslinks in Hydroxylysine–Deficient Collagens of a Heritable Disorder of Connective Tissue," *Proc. Nat. Acad. Sci. USA* 69(9):2594–2598 (Sep. 1972).

Eyre, et al., "Evidence for a previously undetected sequence at the carboxy–terminus of the a1 chain of chicken bone collagen," *Biochemical and Biophysical Research Communications* 48(3):720–726 (1972).

Eyre, et al., "The distribution of crosslinking aldehydes in a1 and a2 chains of chicken bone collagen," *Biochimica et Biophysica Acta* 278:206–210 (1972).

Eyre, et al., "Evidence for intramolecular crosslinks in chicken bone collagen: the isolation of peptides containing allysine aldol," *Biochimica et Biophysica Acta* 295:301–307 (1973).

Eyre, et al., "Analysis of a crosslinked peptide from calf bone collagen: evidence that hydroxylysyl glycoside participates in the crosslinks," *Biochemical and Biophysical Research Communications* 52(2):663–671 (1973).

Eyre, et al., "Isolation of crosslinked peptides from collagen of chicken bone," *Biochem J.* 135:393–403 (1973).

Eyre, et al., "The hydroxypyridinium crosslinks of skeletal collagens: their measurement, properties and a proposed pathway of formation," *Biochemical and Biophysical Research Communications* 92(2):403–410 (1980).

Walters, et al., "Collagen Crosslinks in Human Dentin: Increasing Content of Hydroxypyridinium Residues with Age," *Calcif. Tissue Int.* 35:401–405 (1983).

Wu, et al., "Identification of Hydroxypyridinium Cross–Linking Sites in Type II Collagen of Bovine Articular Cartilage," *Biochemistry* 23:1850–1857 (1984).

Wu, et al., "Cartilage type IX collagen is cross–linked by hydroxypyridinium residues," *Biochemical and Biophysical Research Communications* 123(3):1033–1039 (1984).

Eyre, et al., "Collagen type IX: evidence for covalent linkages to type II collagen in cartilage," *FEB* 220(2):337–341 (1987).

Beardsworth, et al., "Changes with Age in the Urinary Excretion of Lysyl– and Hydroxylysylpyridinoline, Two New Markers of Bone Collagen Turnover," *Journal of Bone and Mineral Research* 5(7):671–676 (1990).

Eyre, D.R., "Collagen: Molecular Diversity in the Body's Protein Scaffold," *Science* 207:1315–1322 (1980).

Eyre, D.R., "Collagen Stability Through Covalent Crosslinking," In: Pearson, et al., eds. *Advances in Meat Research, vol. 4, Collagen as a Food.* New York: Van Nostrand Reinhold, 1987.

Eyre, D.R., "Crosslink maturation in bone collagen," In: Veis, A., ed. the *Chemistry and Biology of Mineralized Connective Tissues*, Elsevier North Holland, Inc., 1981.

Eyre, D.R., "Collagen cross–linking," In: Akeson, W.H. et al., eds., *AAOS: Symposium on Heritable Disorders of Connective Tissue*, St. Louis: C.V. Mosby, 1982, pp. 43–58.

Eyre, et al., "Studies on the molecular diversity and cross–linking of cartilage collagen," In: Peyron, J.G., ed. *Osteoarthritis: Current Clinical and Fundamental Problems*, Paris, France: CIBA–GEIGY, 1984, pp. 117–122.

Delmas, Pierre D., "Biochemical Markers of Bone Turnover for the Clinical assessment of Metabolic Bone Disease," *Endocrinology and Metabolism Clinics of North America*, 19(1) (Mar. 1990).

Uebelhart, et al. "Urinary excretion of pyridinium crosslinks: a new marker of bone resorption in metabolic bone disease" *Bone and Mineral*, 8:87–96 (1990).

Uebelhart, et al., "Effect of Menopause and Hormone Replacement therapy on the Urinary Excretion of Pyridinium Cross–Links," *Journal of Clinical Endocrinology and Metabolism* 72(2):367–373 (1991).

Black, D., Duncan, a. and Robins, S.P., "Quantitative analysis of the Pyridinium Crosslinks of Collagen in Urine Using Ion–Paired Reversed–Phase High–Performance Liquid Chromatography," *analytical Biochemistry* 169: 197–203 (1988).

Hartmann, et al., "Radioimmunoassay of Type I Collagen That Mainly Detects Degradation Products in Serum: Application to Patients with Liver Diseases," *Clin. Chem.*, 36(3):421–426 (1990).

Fujimoto and Moriguchi, "Pyridinoline, a non–reducible crosslink of collagen," *J. Biochem.*, 83:863–867, 1978.

Macek and Adam, Z. *Rheumatol.*, "Determination of collagen degradation products in human urine in osteoarthrosis," 46:237–240, 1987.

Eyre, David R., and Glimcher, Melvin J., "Evidence for Intramolecular Crosslinks in Chicken Bone Collagen, Isolation of Peptides Containing Allysine Aldol," *Chemical Abstracts*, 78: 81202c, 1973.

Kühn, Klaus, "Chemical Properties of Collagen," In: *Immunochemistry of the Extracellular Matrix*, vol. I, pp. 1–29, CRC Press, Inc., 1982.

Robins and Duncan, "Cross–linking of collagen," *Biochem. J.*, 215:175–182 (1983).

Robins, Simon P., and Duncan, Alexander, "Pyridinium crosslinks of bone collagen and their location in peptides isolated from rat femur," *Biochimica et Biophysica Acta*, vol. 914, pp. 233–239.

Henkel, Werner, Glanville, Robert W., and Oreifendorf, Dieter, "Characterisation of type–I collagen trimeric cross–linked peptide from calf aorta and its cross–linked structure," *Eur. J. Biochem*, 165:427–436, 1987.

Hanson, et al., "A specific immunoassay for monitoring human bone resorption: quantitation of type I collagen cross–linked N–telopeptide in urine," *Journal of Bone and Mineral Research*, 7:1251–1258 (1992).

Del Pozo, A.M., et al., "Binding of 1–Anilinonsphthalene–8–Sulfonic Acid to Type I Collagen," *Int. J. Peptide Protein Res.*, 28:329–358, 1983.

Robins, "Analysis of the Crosslinking Components in Collagen and Elastin," *Methods of Biochemical Analysis*, vol. 28, pp. 329–379, John Wiley & Sons, 1982.

Fujimoto, Daisaburo, "Isolation and Characterization of a Fluorescent Material in Bovine Achilles Tendon Collagen," *Biochemical and Biophysical Research Communications*, vol. 76, pp. 1124–1129, 1977.

Seibel, et al., Urinary Hydroxy–pyridinium Crosslinks Provide Indices of Cartilage and Bone Involvement in Arthritic Disease, *The Journal of Rheumatology*, 16(7):964–970 (1989).

Click and Bornstein, Isolation and Characterization of the Cyanogen Bromide Peptides from the α1 and α2 Chains of Human Skin Collagen, *Biochemistry* 9(24):4699–4706 (1970).

Krüger–Franke, M., et al., "Pyridinolinhaltige Kollagenbruchstücke im Urin bei Coxarthrose," *Z. Rheumatol.* 50:323–327 (1991).

Dickson et al., Analysis of the promoter region and the N–propeptide domain of the human proα2(I) collagen gene, *Nucleic Acids Research* 13(10):3427–3438 (1985).

Abbiati et al., Monitoring of free and total urinary pyridinoline and deoxpyridinoline in healthy volunteers: sample relationships between 24–h and fasting early morning urine concentrations, *Bone and Mineral,* 21:9–19 (1993).

Fujimori, Eiji, "Ultraviolet light– and ozone–induced changes in pyridinoline, a trisubstituted 3–hydroxypyridinium crosslink of collagen," *Biochimica et Biophysica Acta,* 828:104–106, 1985.

Sakura, Sachiko, and Fujimoto, Daisaburo, "Photolysis of pyridinoline, a cross–linking amino acid of collagen, by ultraviolet light," *Can. J. Biochem.,* 60:525–529, 1982.

Sakura, Sachiko, and Fujimoto, Daisaburo, "Electrochemical Behaviour of Pyridinoline, a Crosslinking Amino Acid of Collagen," *J. Biochem.,* 89:1541–1546, 1981.

Koob, T.J., Eyre, D.R., and Van Ness, K.P. "Detection and Photolysis of Hydroxypyridinium Cross–links in Cartilage Collagen in situ," *Orthopaedic Transactions,* VII:251–252 (1983).

Rosmalen, F.M.A., Martens, M.F.W.C., van Hoek, M.J.C., et al., "Light Sensitivity of Deoxypyridinoline: Implications for the Collection of Urine," *J. Bone Miner. Res.* 9:B421 (1994).

Baurain, R., Larochelle, J., and Lamy, F. "Photolysis of Desmosine and Isodesmosine by Ultraviolet Light," *Eur. J. Biochem.* 67:155–164, 1976.

Blumsohn, A., Colwell, A., Naylor, K.E., et al., "Effect of Light and gamma–Irradiation on Pyridinoline and Telopeptides of Type I Collagen in Urine," *Clin. Chem.* 41:1195–1197, 1995.

Rauterbrg, J., et al., "Structural Characterization of N–Terminal Antigenic Determinants in Calf and Human Collagen, "*Eur. J. Biochem.,* 27:231–237 (1972).

Furthmayr, H., et al., "Different Antigenic Determinants in the Polypeptide Chains of Human Collagen," *Febs Letters,* 12(6):341–344.

Becker, U., Timpl, R., and Kuhn, K. "Carboxyterminal Antigenic Determinants of Collagen from Calf Skin: Localization within Discrete Regions of the Nonhelical Sequences," *Eur. J. Biochem.* 28:221–231 1972.

Timpl, R., et al., "Maturation of the Immune Response to Soluble Rat Collagen: Late Appearance of Antibodies Directed to N–Terminal Sites of the α2–Chain," *The Journal of Immunology,* 108(1):119–125 (1972).

Kuhn, K. "The Classical Collagens: Types I, II, and III," In: *Structure and Function of Collagen Types,* (1987).

Rauterberg, J. "The C–Terminal Non–Helical Portion of the Collagen Molecule," *Clin. Ortho. Rel. Res.* 97:196–212 1973.

Davril, M., Han, K., Guay, M., et al., "Photolysis of Crosslinked Peptides from Elastin of Porcine Aorta," *FEBS Lett.* 98:128–134 1979.

Otter, A., Scott, P.G., and Kotovych, G. "Type I Collagen a–1 Chain C–Telopeptide: Solution Structure Determined by 600–MHz Proton NMR Spectroscopy and Implications for Its Role in Collagen Fibrillogenesis," *Biochemistry,* 27:3560–3567 1988.

van Hoek, M.J.C., Martens, M.F.W.C., Walchli, R., et al., "A Novel Polyclonal Antibody Against Deoxy–Pyridinoline to be used in a Radioimmunoassay," (1994).

Fuller, F. and Boedtker, H. "Sequence Determination and Analysis of the 3' Region of Chicken Pro–a1(I) and Pro–a __(I) Collagen Messenger Ribonucleic Acids Including the Carboxy–Terminal Propeptide Sequences," *Biochemistry,* 20:996–1006 1981.

Rosmalen, F.M.A., Martens, M.F.W.C., van Hoek, M.J.C., et al., "Light Sensitivity of Deoxypyridinoline: Implications for the Collection of Urine," (1994).

Gunja–Smith & Boucek, "Desmosines in human urine," *Biochem. J.,* 193:915–918, 1981.

Tellerova et al., "Determination of larger urinary peptides in osteoarthrosis by high–performance liquid chromatography," *Scand J Rheumatology* 15:52–56 (1986).

Adam, M. and Deyl, Z., "Altered expression of collagen phenotype in osteoarthrosis," *Clinica Chimica Acta.,* 133:25–32 (1983).

Johnstone et al., Immunochemistry in Practice, Blackwell Scientific Publications, Oxford, U.K., 1987, pp. 48–65.

Davison, et al., "The Effects of Acetic Acid on Collagen Cross–Links," *Connective Tissue Research* 1:205–216 (1972).

Robins, "Cross–linking of collagen," *Biochem. J.* 215:167–173 (1983).

Kuivaniemi, et al., "Structure of a full–length cDNA clone for a preproα(I) chain of human type I procollagen," *Biochem. J.* 252:633–640 (1988).

Bernard, M.P. et al., "Nucleotide sequences of complementary deoxyribonucleic acids for the proα$_1$ chain of human type I procollagen. Statistical evaluation of structures that are conserved during evolution," *Biochemistry* 22:5213–5223 (1983).

Lane et al., "Immunofluorescent Localization of Structural Collagen Types in Endochondral Fracture Healing," *Orthopaedic Transactions,* VI(2):236 (1982).

Hassager et al., "The carboxy–terminal pyridinoline cross–linked telopeptide of type I collagen in serum as a marker of bone resorption: the effect of nandroline decanoate and hormone replacement therapy," *Calcif Tissue Int* 54:30–33 (1994).

Gerz et al., "Monitoring bone resorption in early postmenopausal women by an immunoassay for cross–linked collagen peptides in urine," JMBMR 9:135–142 (1994).

Robins, "Collagen crosslinks in metabolic bone disease," *Acta Orthop Scand* 66:171–175 (1995).

Eyre, "The specificity of collagen cross–links as markers of bone and connective tissue degradation," *Acta Orthop Scand* 66:166–170 (1995).

Hanson & Eyre, "Molecular site specificity of pyridinoline and pyrrole cross–links in type I collagen of human bone," JBC 271:26508–26516 (1996).

Kivirikko, "Urinary excretion of hydroxyproline in health and disease," *Int Rev Connect Tissue Res* 5:93–163 (1970).

Garnero et al., "Markers of bone resorption predict hip fracture in elderly women: the EPIDOS prospective study," JMBMR 11:1531–1538 (1996).

McClung et al., "Inability of baseline biochemical markers to predict bone density changes in early postmenopausal women," JMBMR 11(Suppl.1):S127, Abstract 129.

Furthmayer, *Immunochemistry of the Extracellular Matrix, vol. 1—Methods,* "Immunization procedures, isolation by affinity chromatography, and serological and immunochemical characterization of collagen specific antibodies," CRC Press, pp. 143–178 (1982).

Sambrook & Reeve, "Bone density in rheumatoid arthritis," *Clinical Science* 74:225–230 (1988).

Alwan et al., "Bone resorbing activity in synovial fluids in destructive osteoarthritis and rheumatoid arthritis," *Annals of the Rheumatic Diseases* 47:198–205 (1988).

DETECTION OF TYPE 1 COLLAGEN DEGRADATION IN VIVO

This application is a continuation of Ser. No. 08/561,842, filed Nov. 22, 1995 U.S. Pat. No. 5,688,652, which in turn is a contuation of Ser. No. 08/229,569 filed Apr. 19, 1994 now U.S. Pat. No. 5,472,884, which in turn is a continuation of Ser. No. 07/708,529 filed May 31, 1991, now U.S. Pat. No. 5,320,970, which in turn is a continuation-in-part of Ser. No. 07/614,719 filed Nov. 21, 1990 now U.S. Pat. No. 5,300,434, which in turn is a continuation-in-part of Ser. No. 07/444,881 filed Dec. 1, 1989, now U.S. Pat. No. 5,140,103, which in turn is a continuation-in-part of Ser. No. 07/118, 234 filed Nov. 6, 1987, now U.S. Pat. No. 4,973,666.

This invention was made with government support under grants AR37318 and AR36794 awarded by the National Institutes of Health. The government has certain rights in the invention.

FIELD OF THE INVENTION

The present invention relates to methods for detecting and monitoring collagen degradation in vivo. More specifically, it relates to methods for quantitating certain cross-linked telopeptides produced in vivo upon degradation of collagen and to reagents useful in such methods.

BACKGROUND OF THE INVENTION

Three known classes of collagens have been described to date. The Class I collagens, subdivided into types I, II, III, V, and XI, are known to form fibrils. These collagens are all synthesized as procollagen molecules, made up of N-terminal and C-terminal propeptides, which are attached to the core collagen molecule. After removal of the propeptides, which occurs naturally in vivo during collagen synthesis, the remaining core of the collagen molecule consists largely of a triple-helical domain having terminal telopeptide sequences which are nontriple-helical. These telopeptide sequences have an important function as sites of intermolecular cross-linking of collagen fibrils extracellularly.

The present invention relates to methods of detecting collagen degradation based on assaying for particular cross-linked telopeptides produced in vivo upon collagen degradation. In the past, assays have been developed for monitoring degradation of collagen in vivo by measuring various biochemical markers, some of which have been degradation products of collagen. For example, bone turnover associated with Paget's disease has been monitored by measuring small peptides containing hydroxyproline, which are excreted in the urine following degradation of bone collagen. Russell et al., *Metab. Bone Dis. and Rel. Res.* 4 and 5, 255–262 (1981); and Singer, F. R., et al., *Metabolic Bone Disease*, Vol. 11 (eds. Avioli, L. V. and Kane, S. M.), 489–575 (1978), Academic Press, New York.

Other researchers have measured the cross-linking compound pyridinoline in urine as an Index of collagen degradation in joint disease. See, for background and for example, Wu and Eyre, *Biochemistry*, 23:1850 (1984); Black et al., *Annals of the Rheumatic Diseases*, 48:641–644 (1989); Robins et al.; *Annals of the Rheumatic Diseases*, 45:969–973 (1986); and Seibel et al., *The Journal of Rheumatology*, 16:964 (1989). In contrast to the present invention, some prior researchers have hydrolyzed peptides from body fluids and then looked for the presence of individual hydroxypyridinium residues. None of these researchers has reported measuring a telopeptide containing a cross-link that is naturally produced in vivo upon collagen degradation, as in the present invention.

U.K. Patent application GB 2,205,643 reports that the degradation of type III collagen In the body is quantitatively determined by measuring the concentration of an N-terminal telopeptide from type III collagen in a body fluid. In this reference, it is reported that cross-linked telopeptide regions are not desirable. In fact, this reference reports that it is necessary to use a non-cross-linked source of collagen to obtain the telopeptide. The peptides of the present invention are all cross-linked. Collagen cross-links are discussed in greater detail below, under the heading "Collagen Cross-Linking."

There are a number of reports indicating that collagen degradation can be measured by quantitating certain procollagen peptides. The present invention involves telopeptides rather than propeptides, the two being distinguished by their location in the collagen molecule and the timing of their cleavage in vivo. See U.S. Pat. No. 4,504,587; U.S. Pat. No. 4,312,853; Pierard et al., *Analytical Biochemistry* 141:127–136 (1984); Niemela, *Clin. Chem.*, 31/8:1301–1304 (1985); and Rohde et al., *European Journal of Clinical Investigation*, 9:451–459 (1979).

U.S. Pat. No. 4,778,768 relates to a method of determining changes occurring in articular cartilage involving quantifying proteoglycan monomer or antigenic fragments thereof in a synovial fluid sample. This patent does not relate to detecting cross-linked telopeptides derived from degraded collagen.

Dodge, *J. Clin. Invest.*, 83:647–661 (1981) discloses methods for analyzing type II collagen degradation utilizing a polyclonal antiserum that specifically reacts with unwound alpha-chains and cyanogen bromide-derived peptides of human and bovine type It collagens. The peptides involved are not cross-linked telopeptides as in the present invention.

Amino acid sequences of human type III collagen, human proα(II) collagen, and the entire preproα1(III) chain of human type III collagen and corresponding cDNA clones have been investigated and determined by several groups of researchers. See Loidl et al., *Nucleic Acids Research* 12:9383–9394 (1984); Sangiorgi et al., *Nucleic Acids Research*, 13:2207–2225 (1985); Baldwin et al., Biochem. J., 262:521–528 (1989); and Ala-Kokko et al., *Biochem. J.*, 260:509–516 (1989). None of these references specifies the structures of particular telopeptide degradation products that could be measured to determine the amount of degraded fibrillar collagen in vivo.

In spite of the above-described background information, there remains a need for effective and simple assays for determining collagen degradation in vivo. Such assays could be used to detect and monitor disease states in humans, such as osteoarthritis (type II collagen degradation), and various inflammatory disorders, such as vasculitis syndrome (type III collagen degradation).

Assays for type I collagen degradation, described in a parent application, U.S. Ser. No. 118,234, can be utilized to detect and assess the rate of bone resorption in vivo. Detection of the rate of bone resorption may be a factor of interest in monitoring and detecting diseases such as osteoporosis. Osteoporosis is the most common bone disease in man. Primary osteoporosis, with increased susceptibility to fractures, results from a progressive net loss of skeletal bone mass. It is estimated to affect 15–20 million individuals in the United States. Its basis is an age-dependent imbalance in bone remodeling, i.e., in the rates of synthesis and degradation of bone tissue.

About 1.2 million osteoporosis-related fractures occur in the elderly each year including about 538,000 compression fractures of the spine, about 227,000 hip fractures and a substantial number of early fractured peripheral bones. Twelve to 20% of the hip fractures are fatal because they cause severe trauma and bleeding, and half of the surviving patients require nursing home care. Total costs from osteoporosis-related injuries now amount to at least $7 billion annually (Barnes, O. M., *Science*, 236:914 (1987)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, no method is available for measuring bone resorption rates in patients or normal subjects. A major difficulty in monitoring the disease is the lack of a specific assay for measuring bone resorption rates.

Methods for assessing bone mass often rely on measuring whole-body calcium by neutron activation analysis or mineral mass in a given bone by photon absorption techniques. These measurements can give only long-term impressions of whether bone mass is decreasing. Measuring calcium balances by comparing intake with output is tedious, unreliable and can only indirectly appraise whether bone mineral is being lost over the long term. Other methods currently available for assessing decreased bone mass and altered bone metabolism include quantitative scanning radiometry at selected bone locations (wrist, calcaneus, etc.) and histomorphometry of iliac crest biopsies. The former provides a crude measure of the bone mineral content at a specific site in a single bone. Histomorphometry gives a semi-quantitative assessment of the balance between newly deposited bone seams and resorbing surfaces.

A urinary assay for the whole-body output of degraded bone in 24 hours would be much more useful. Mineral studies (e.g., calcium balance) cannot do this reliably or easily. Since bone resorption involves degradation of the mineral and the organic matrix, a specific biochemical marker for newly degraded bone products in body fluids would be the ideal index. Several potential organic indices have been tested. For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as pointed out above. For this reason, urinary hydroxyproline has been used extensively as an amino acid marker for collagen degradation. Singer, F. R., et al. (1978), cited hereinabove.

U.S. Pat. No. 3,600,132 discloses a process for determination of hydroxyproline In body fluids such as serum, urine, lumbar fluid and other intercellular fluids In order to monitor deviations in collagen metabolism. In particular, this Inventor notes that in pathologic conditions such as Paget's disease, Marfan's syndrome, osteogenesis imperfecta, neoplastic growth in collagen tissues and in various forms of dwarfism, increased collagen anabolism or catabolism as measured by hydroxyproline content in biological fluids can be determined. This inventor measures hydroxyproline by oxidizing it to a pyrrole compound with hydrogen peroxide and N-chloro-p-toluenesulphonamide followed by colorimetric determination in -dimethyl-amino-benzaldehyde.

In the case of Paget's disease, the increased urinary hydroxyproline probably comes largely from bone degradation; hydroxyproline, however, generally cannot be used as a specific Index. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline. Furthermore, about 80% of the free hydroxyproline derived from protein degradation is metabolized in the liver and never appears in the urine. Kiviriko, K. I. *Int. Rev. Connect. Tissue Res.* 5:93 (1970), and Weiss, P. H. and Klein, L., *J. Clin. Invest.* 48:1 (1969).

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally nonspecific markers of bone resorption. Krane, S. M. and Simon, L. S. *Develop. Biochem.*, 22:185 (1981).

In addition to amino acids unique to collagen, various non-collagenous proteins of bone matrix such as osteocalcin, or their breakdown products, have formed the basis of immunoassays aimed at measuring bone metabolism. Price, P. A. et al. *J. Clin. Invest.,* 66:878 (1980), and Gundberg, C. M. et al., *Meth. Enzymol.*, 107:516 (1984). However, it is now clear that bone-derived noncollagenous proteins, though potentially a useful index of bone metabolic activity are unlikely, on their own, to provide quantitative measures of bone resorption. The concentration in serum of osteocalcin, for example, fluctuates quite widely both normally and in metabolic bone disease. Its concentration is elevated in states of high skeletal turnover but it is unclear whether this results from increased synthesis or degradation of bone. Krane, S. M., et al., *Develop. Biochem.*, 22:185 (1981), Price, P. A. et al.,*J. Clin. Invest.*, 66:878 (1980); and Gundberg, C. M. et al., *Meth. Enzymol.*, 107:516 (1984).

Collagen Cross-Linking

The polymers of most genetic types of vertebrate collagen require the formation of aldehyde-mediated cross-links for normal function. Collagen aldehydes are derived from a few specific lysine or hydroxylysine side-chains by the action of lysyl oxidase. Various di-, tri- and tetrafunctional cross-linking amino acids are formed by the spontaneous intra- and intermolecular reactions of these aldehydes within the newly formed collagen polymers; the type of cross-linking residue varies specifically with tissue type (see Eyre, D. R. et al., *Ann. Rev. Biochem.*, 53:717–748 (1984)).

Two basic pathways of cross-linking can be differentiated for the banded (67 nm repeat) fibrillar collagens, one based on lysine aldehydes, the other on hydroxylysine aldehydes. The lysine aldehyde pathway dominates in adult skin, cornea, sclera, and rat tail tendon and also frequently occurs in other soft connective tissues. The hydroxylysine aldehyde pathway dominates in bone, cartilage, ligament, most tendons and most internal connective tissues of the body, Eyre, D. R. et al. (1984) vida supra. The operating pathway is governed by whether lysine residues are hydroxylated in the telopeptide sites where aldehyde residues will later be formed by lysyl oxidase (Barnes, M. J. et al., *Biochem. J.*, 139:461 (1974)).

The chemical structure(s) of the mature cross-linking amino acids on the lysine aldehyde pathway are unknown, but hydroxypyridinium residues have been identified as mature products on the hydroxylysine aldehyde route. On both pathways and in most tissues the intermediate, borohydride-reducible cross-linking residues disappear as the newly formed collagen matures, suggesting that they are relatively short-lived intermediates (Bailey, A. J. et al., FEBS Lett., 16:86 (1971)). Exceptions are bone and dentin, where the reducible residues persist in appreciable concentration throughout life, in part apparently because the rapid mineralization of the newly made collagen fibrils inhibits further spontaneous cross-linking interactions (Eyre, D. R., In: *The Chemistry and Biology of Mineralized Connective Tissues*, (Veis, A. ed.) pp. 51–55 (1981), Elsevier, N.Y., and Walters, C. et al., *Calc. Tiss. Intl.*, 35:401–405 (1983)).

Two chemical forms of 3-hydroxypyridinium cross-link have been identified (Formula I and II). Both compounds are naturally fluorescent, with the same characteristic excitation and emission spectra (Fujimoto, D. et al. *Biochem. Biophys. Res. Commun.*, 76:1124 (1977), and Eyre, D. R., *Develop. Biochem.*, 22:50 1981)). These amino acids can be resolved and assayed directly in tissue hydrolysates with good sensitivity using reverse phase HPLC and fluorescence detection. Eyre, D. R. et al., *Analyte. Biochem.*, 137:380–388 (1984). It should be noted that the present invention involves quantitating particular peptides rather than amino acids.

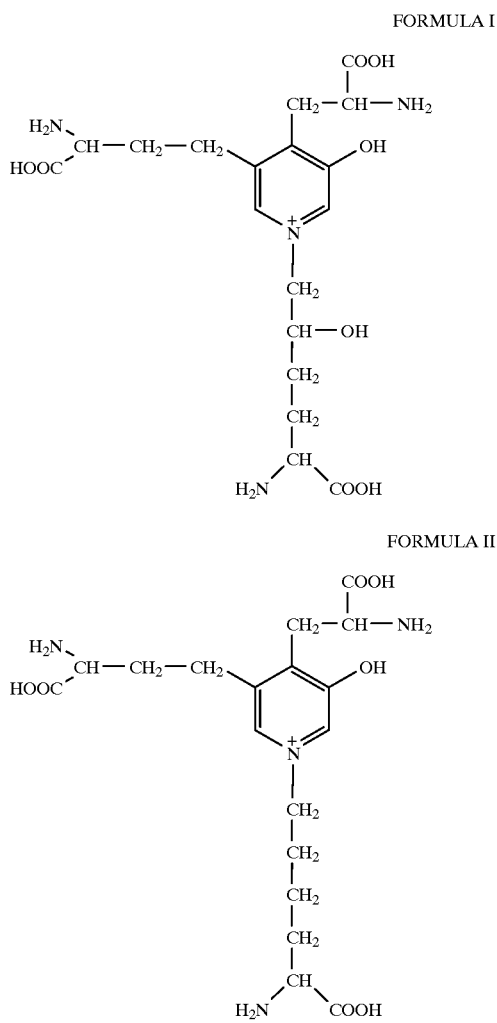

In growing animals, it has been reported that these mature cross-links may be concentrated more in an unmineralized fraction of bone collagen than in the mineralized collagen (Banes, A. J., et al., *Biochem. Biophys. Res. Commun.*, 113:1975 (1983). However, other studies on young bovine or adult human bone do not support this concept, Eyre, D. R., In: *The Chemistry and Biology of Mineralized Tissues* (Butler, W. T. ed.) p. 105 (1985), Ebsco Media Inc., Birmingham, Ala.

The presence of collagen hydroxypyridinium cross-links in human urine was first reported by Gunja-Smith and Boucek (Gunja-Smith, Z. and Boucek, R. J., *Biochem J.*, 197:759–762 (1981)) using lengthy isolation procedures for peptides and conventional amino acid analysis. At that time, they were aware only of the HP form of the cross-link. Robins (Robins, S. P., *Biochem J.*, 207:617–620 (1982) has reported an enzyme-linked immunoassay to measure HP in urine, having raised polyclonal antibodies to the free amino acid conjugated to bovine serum albumin. This assay is intended to provide an index for monitoring increased joint destruction that occurs with arthritic diseases and is based, according to Robins, on the finding that pyridinoline is much more prevalent in cartilage than in bone collagen.

In more recent work involving enzyme-linked immunoassay, Robins reports that lysyl pyridinoline is unreactive toward antiserum to pyridinoline covalently linked to bovine serum albumin (Robins et al., *Ann. Rheum. Diseases*, 45:969–973 (1986)). Robins'urinary index for cartilage destruction is based on the discovery that hydroxylysyl pyridinoline, derived primarily from cartilage, is found in urine at concentrations proportional to the rate of joint cartilage resorption (i.e., degradation). In principle, this index could be used to measure whole body cartilage loss; however, no information on bone resorption would be available.

A need therefore exists for a method that allows the measurement of whole-body bone resorption rates in humans. The most useful such method would be one that could be applied to body fluids, especially urine. The method should be sensitive, i.e., quantifiable down to 1 picomole and rapidly measure 24-hour bone resorption rates so that the progress of various therapies (e.g., estrogen) can be assessed.

Prior U.S. Ser. Nos. 614,719, 444,881 and 118,234, which are hereby incorporated by reference herein, disclosed particular peptides, methods of assaying for collagen degradation based on detecting these peptides, and kits useful for practicing the methods. Additionally, U.S. Ser. No. 614,719 disclosed a particular monoclonal antibody MAb-1H11 that is capable of binding to a peptide having the following structure:

FORMULA III

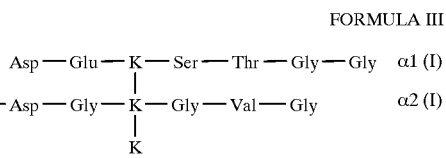

where

is hydroxylysyl pyridinoline (HP) or lysyl pyridinoline (LP), and Gln is glutamine or pyrrolidone carboxylic acid, and other peptides that contain the same binding epitope. The present invention is based on these prior discoveries, but provides additional previously undisclosed elements thereof.

SUMMARY OF THE INVENTION

In a first embodiment, the present invention provides certain novel peptides derived from type I collagen that are produced in vivo and that may be found in body fluids. These peptides are recognized and bound by the antibody MAb-1H11. Structures of the peptides have been determined and/or verified by electrospray mass spectrometry (using a SCIEX instrument). The structures of the peptides isolated from urine using MAb-1H11 are reported hereinbelow in the description of FIG. 1, and include the type I collagen peptide having the formula reported previously in U.S. Pat. No. 4,973,666, as well as some relatively minor variants thereof. Additionally, a previously unknown peptide was discovered in urine using this affinity chromatography technique. This peptide, corresponding to peak D in FIG. 1, and having the structure provided in the description of FIG. 1 below, is a peptide composed of two segments of α(2) chains of collagen. The first aspect of the present invention relates to this dimeric peptide, methods of analyzing collagen degradation, which is correlated to the rate of bone resorption, based on quantitating the peptide, and kits for such quantitation.

A second embodiment of the present invention relates to compositions for use in quantitating cross-linked collagen telopeptides derived from type I collagen. It has been discovered that protease treatment of collagen from bone, followed by purification of the collagen fragments to enrich the mixture in an epitope that is specifically recognized by the antibody MAb-1H11, results in a composition that can be used in an assay for type I collagen telopeptides that occur in vivo in body fluids. Thus, this aspect of the invention is directed to a composition of collagen peptides derived from protease treatment of bone, to methods employing the composition in quantitation of type I collagen telopeptides, and to kits that include such compositions in solution, lyophilized, or coated on a solid support.

These and other aspects of the present invention will be described in greater detail hereinbelow.

A: FORMULA IV

Figure 1:
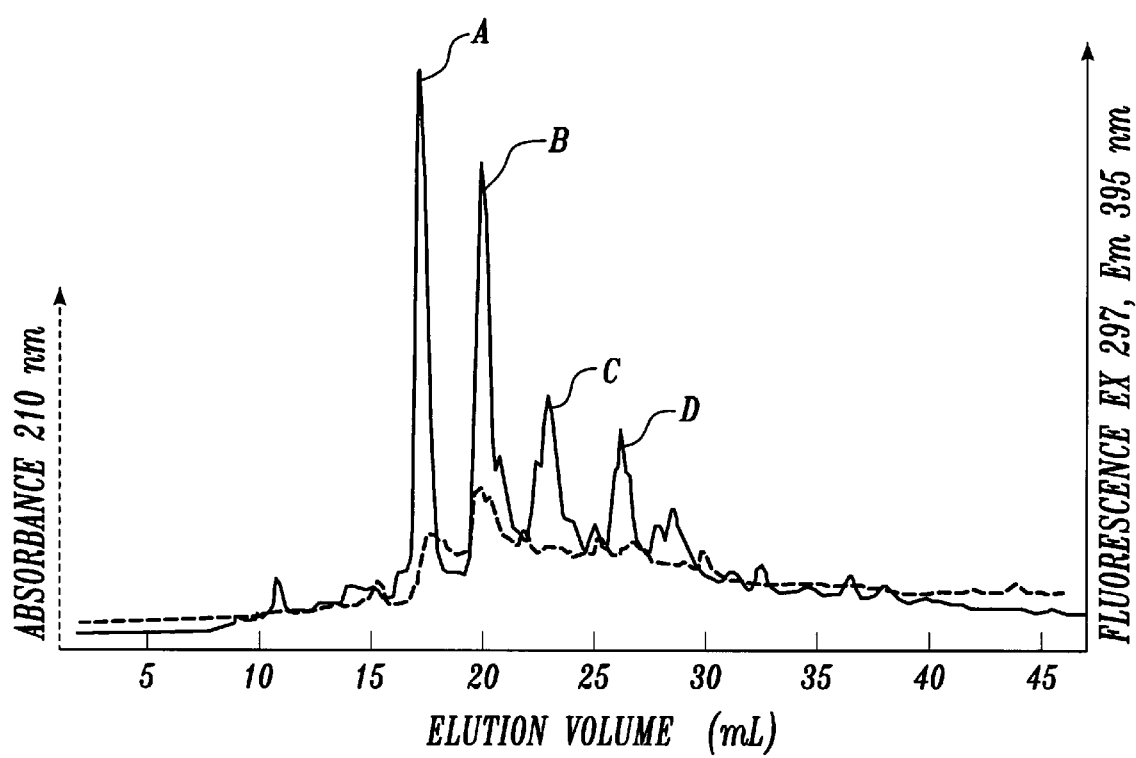
FIG. 1 depicts an elution profile of peptides isolated by affinity chromatography from human urine. The structures of the peptides, as determined by mass spectrometry, are as follows.

Asp — Glu — K — Ser — Thr — Gly — (Gly)
J — Tyr — Asp — Gly — K — Gly — Val — Gly
                    |
                    K

FORMULA V

Tyr — Asp — Glu — K — Ser — Thr — Gly — (Gly)
J — Tyr — Asp — Gly — K — Gly — Val — Gly
                    |
                    K
+

B: FORMULA VI

Asp — Glu — K — Ser — Thr — Gly — (Gly)
J — Tyr — Asp — Gly — K — Gly — Val — Gly — Leu
                    |
                    K

C: FORMULA VII

Tyr — Asp — Glu — K — Ser — Thr — Gly — (Gly)
J — Tyr — Asp — Gly — K — Gly — Val — Gly — Leu
                    |
                    K

D: FORMULA VIII

J — Tyr — Asp — Gly — K — Gly — Val — Gly — (Leu)
J — Tyr — Asp — Gly — K — Gly — Val — Gly — (Leu)
                    |
                    K wherein J represents pyroglutamic acid or glutamine and the parentheses indicate that an amino acid may or may not be present.

DETAILED DESCRIPTION OF THE PREFERRED EMBODIMENTS

Cross-Linked Peptides

A first embodiment of the present invention relates to cross-linked peptides isolatable from urine that are derived from type I collagen and are released when bone is resorbed in vivo. These peptides occur naturally in body fluids, such as urine, and may be isolated by standard purification protocols. The purified peptides may be used, for example, as antigens to produce immunological binding partners thereto. A preferred purification protocol employs the antibody MAb-1H11. The hybridoma (1H11) that produces this preferred monoclonal antibody has been deposited at the American Type Culture Collection (ATCC), 12301 Parklawn Drive, Rockville, Md. 20852, under accession No. HB 10611. Purification of these peptides by affinity chromatography using monoclonal antibodies produced by 1H11 results in highly purified bone-type I collagen cross-linked N-telopeptides, as shown in FIG. 1.

A particularly interesting peptide isolated in this manner corresponds to peak D in FIG. 1, which has the following structure:

FORMULA VIII

J — Tyr — Asp — Gly — K — Gly — Val — Gly — (Leu)
J — Tyr — Asp — Gly — K — Gly — Val — Gly — (Leu)
                    |
                    K wherein J is pyroglutamic acid or glutamine (Leu) means optional leucines (i.e., either leucine may be present, both leucines may be present, or neither leucine may be present), and the cross-linking amino acid HP or LP is represented by the connected K residues. Although the above structure covers several peptides, for convenience, the following discussion refers to a single peptide.

This structure is surprising in that it implies that it is derived from three entirely separate collagen molecules that are cross-linked together. There has been some controversy In the scientific literature as to whether cross-linking of collagen molecules occurs intramolecularly or intermolecularly. The structure of the above dimeric peptide supports the latter view.

In more practical terms, the above-described peptide may be used in an assay for the rate of bone resorption. Under these circumstances, the procedures, techniques, kits, etc., disclosed in the prior related applications, which have been incorporated by reference above, may be employed analogously with this peptide.

A preferred method of quantitating this peptide (and its equivalents) employs an immunological binding partner thereto. The peptide is utilized as an antigen, either alone or conjugated to a carrier molecule to produce antibodies, which may be polyclonal or monoclonal, or binding fragments thereof. Binding fragments may also be produced recombinantly, if desired. Monoclonal antibodies are preferred. An especially preferred monoclonal antibody is that produced by 1H11, described herein. The amount of this peptide in a body fluid may be correlated directly to the absolute rate of bone resorption, or the level of this peptide may be correlated to other type I collagen peptides that occur in greater quantities, which in turn may be correlated to the absolute rate of bone resorption. A kit containing reagents, etc., for quantitating this peptide is also contemplated in accordance with the present invention. These kits would typically include containers of appropriate reagents, such as Immunological binding partners to the above-described peptide, suitable controls, competitive binding reagents, and the like. Any other standard method of peptide quantitation may also be employed for these purposes. Kits for carrying out such methods are also contemplated.

By analogy to the disclosure incorporated herein from prior U.S. Ser. No. 614,719, the pyridinoline ring contained in the above-described peptide may be open or closed. An assay based on quantitating either form or both forms of the peptide, and kits for carrying out the assay, are also contemplated.

In addition to the dimeric peptide described above, additional peptides corresponding to Formula III in U.S. Ser. No. 118,234, now issued as U.S. Pat. No. 4,973,666, are also isolatable from urine. These peptides illustrate the fact that a small number of amino acids (e.g., 1–3) may be attached to the N or C termini of the peptides in body fluids. For example, the peptides of Formula III may have a Tyr residue attached to the N-terminal of the α1 (I) chain. Also, the peptide corresponding to peak A in FIG. 1 is an equivalent of the peptides contained in peaks B and C. Analogously, the peptide falling within peak D is also expected to have equivalent peptides in which one or a small number of amino acids are combined with the N or C termini thereof. These amino acids will typically correspond to the amino acids normally found in type I collagen molecules in vivo. The language "consisting essentially of" includes such peptide equivalents.

Isolation of Type I Collagen Telopeptides

Urine from patients with active Paget's disease is dialyzed in reduced porosity dialysis tubing (<3,500 mol. wt. cut off Spectropore) at 4° C. for 48 h to remove bulk solutes. Under these conditions the peptides of interest are largely retained. The freeze-dried non-diffusate is then eluted (200 mg aliquots) from a column (90 cm×2.5 cm) of Bio-Gel P2 (200–400 mesh) in 10% acetic acid at room temperature. A region of effluent that combines the cross-linked peptides is defined by measuring the fluorescence of collected fractions at 297 nm excitation/395 nm emission, and this pool is freeze-dried. Further resolution of this material is obtained on a column of Bio-Gel P-4 (200–400 mesh, 90 cm×2.5 cm) eluted in 10% acetic acid.

Two contiguous fraction pools are defined by monitoring the fluorescence of the eluant above. The earlier fraction is enriched in peptide fragments having two amino acid sequences that derive from the C-terminal telopeptide domain of the α1 (I) chain of bone type I collagen linked to a third sequence derived from the triple-helical body of bone type I collagen. These three peptide sequences are cross-linked with 3-hydroxypyridinium. The overlapping later fraction is enriched in peptide fragments having an amino acid sequence that is derived from the N-terminal telopeptide domain of bone type I collagen linked through a 3-hydroxypyridinium cross-links.

Individual peptides are then resolved from each of the two fractions obtained above by ion-exchange HPLC on a TSK DEAE-5-PW column (Bio Rad 7.5 cm×7.5 mm) eluting with a gradient of NaCl (0–0.2M) in 0.02M Tris-HCl, pH 7.5 containing 10% (v/v) acetonitrile. The N-terminal telopeptide-based and C-terminal telopeptide-based cross-linked peptides elute in a series of 3–4 peaks of fluorescence between 0.08M and 0.15M NaCl. The C-terminal telopeptide-based cross-linked peptides elute first as a series of fluorescent peaks, and the major and minor N-terminal telopeptide-based cross-linked peptides elute towards the end of the gradient as characteristic peaks. Each of these is collected, freeze-dried and chromatographed on a C-18 reverse phase HPLC column (Vydac 218TP54, 25 cm×4.6 mm) eluted with a gradient (0–10%) of acetonitrile: N-propanol (3:1 v/v) in 0.01M trifluoroacetic acid. About 100–500 μg of individual peptide fragments containing 3-hydroxypyridinium cross-links can be isolated by this procedure from a single 24 h collection of Paget's urine.

Amino acid compositions of the major isolated peptides confirmed purity and molecular sizes by the whole number stoichiometry of recovered amino acids. N-terminal sequence analysis by Edman degradation confirmed the basic core structures corresponding to the sequences of the known cross-linking sites in type I collagen and from the matching amino acid compositions. The N-terminal telopeptide sequence of the α2(I) chain was blocked from sequencing analysis due presumably to the known cyclization of the N-terminal glutamine to pyrrolidone carboxylic acid.

A preferred method of isolating the peptides described above, and schematically shown in FIG. 1, will now be described:

Affinity-column Purification of Cross-linked N-telopeptides from Human Bone Collagen 1. Preparation of Column Monoclonal antibody (MAb) 1H11 was coupled to CNBr-activated Sepharose® (Pharmacia) by conventional methods (manufacturer's protocol). Mouse ascites fluid (3 ml) containing MAb 1H11 was adsorbed on a Protein G-Sepharose® affinity column diluted (1:1 v/v) in 0.15M NaCl, 0.025M Tris-HCl (TBS), pH 7.5. After washing in the same buffer, IgG was eluted by 0.1M glycine-HCl, pH 2.5, dialysed against the coupling buffer and coupled to activated Sepharose®.

2. Binding and Elution of Urinary Peptides

Urine (17-year adolescent, male) was diluted with TBS, pH 7.5 (1:1 v/v) and eluted dropwise at 25° C. through the 1H11affinity column (5 ml bed volume). After washing with TBS, bound peptides were eluted with 50% saturated ammonium sulfate containing 1% (v/v) trifluoroacetic acid (TFA). The eluted peptides were passed through a pre-conditioned C18-Sep-Pak (Waters), bound peptides were eluted with 50% (v/v) acetonitrile and dried. Individual peptides were resolved by reverse-phase HPLC (C8, RP-300 Brownlee) using an acetonitrile:n-propanol (3:1 v/v) gradient in aqueous 0.1% (v/v) TFA. Highly purified bone type I collagen cross-linked N-telopeptides were recovered (see FIG. 1).

Protease-Generated Compositions

A second embodiment of the present invention relates to compositions comprising peptides derived from bone collagen by treatment thereof with a protease in vitro. One preferred protease is collagenase. Such compositions should contain peptide fragments that include the epitope recognized by the monoclonal antibody produced by 1H11. It is preferred that the compositions be enriched in such epitopes by purification (discussed below). The resulting compositions are useful in carrying out assays to quantitate collagen-derived peptides that are produced in vivo as described above. For example, a composition containing epitope-enriched collagenase-produced peptide fragments may be coated on a solid substrate (e.g., a microtiter assay plate) to be used in a heterogeneous competitive immunoassay. Since these peptides are expected to be relatively hydrophilic, coating them on a relatively hydrophobic solid surface may require conjugation of the peptides In the composition to a carrier molecule, such as bovine serum albumin, which will enhance adsorption onto a solid substrate.

The peptides of these compositions may also be useful in a homogeneous competitive immunoassay In solution by labeling the peptides with a detectable marker. Examples of suitable detectable markers include, but are not limited to: enzymes, co-enzymes, enzyme inhibitors, chromophores, fluorophores, phosphorescent materials, chemiluminescent materials, paramagnetic metals, spin labels, avidin/biotin, and radionuclides. The peptide mixtures produced by protease digestion (labeled or unlabeled) can be provided in solution (preferably having a concentration of 1 to 100 picomoles of peptide structures containing 1H11 epitope per milliliter) and included in a kit. These labeled peptides compete with naturally occurring peptide fragments in a body fluid for binding to a suitable binding partner. Such compositions may also be used as a control solution in an assay, enabling calibration in terms of units of bone collagen. The solutions may contain salts and other standard ingredients to stabilize or preserve them. Preferably, phosphate or Tris buffered saline will be used. It is also possible to provide the protease generated compositions in solid (e.g., lyophilized) form.

Any of various standard types of immunoassays can be utilized to measure the concentration of the collagen-derived peptides contained in a body fluid. Many of these assays will be compatible with the protease generated compositions described herein. One specific assay involves coating 1H11 antibody on a solid substrate and employing this coated antibody to bind to a target peptide in a body fluid, in the presence of a standard amount of a protease generated peptide composition. A labeled second antibody specific to an epitope only present on the protease-generated peptides could then be used to detect bound non-target peptide(s). A greater amount of detected labeled antibody would mean less target peptide in the body fluid.

By "enriched" is meant that the protease-generated composition is partially purified to increase the amount of epitopes recognized by 1H11 contained in the composition. It is known that bone collagen consists of approximately 0.1% by weight of the peptides of FORMULAS IV–VIII, which contain the 1H11 epitopes.

Theoretically, therefore, it can be calculated that the maximum possible enrichment (corresponding to completely purified 1H11 epitope) is 1000-fold. This degree of purification could be achieved by affinity chromatography using bound 1H11 antibody. Lesser degrees of enrichment, e.g., 10-fold to 50-fold, may be achieved by HPLC or other standard purification protocols. Preferably, the enrichment of 1H11 epitopes will be at least about 10-fold. Particularly preferably, the enrichment will be at least about 50-fold. The degree of enrichment may be verified by testing a sample of the preparation with an affinity column containing 1H11 monoclonal antibodies and determining the amount of material retained on the column as a percentage of the amount of material introduced into the column.

To produce the above-described compositions of this invention, it is necessary to contact protease, preferably bacterial collagenase, with bone collagen for a period of time sufficient to produce peptide fragments from the bone collagen. Preferably, bone will be finely powdered and demineralized before contacting it with collagenase. See, for example, Wu, J-J. and Eyre, D. R., "Fine Powdering Exposes the Mineral-Protected Collagen of Bone to Protease Digestion,", *Calcif. Tissue Int.*, 42:243–247 (1988).

Other proteases that can produce peptide fragments capable of being bound by 1H11 could also be used. A given protease may be screened by allowing it to contact bone collagen and then determining if the fragments that are generated bind to 1H11.

Collagenase may be obtained from commercial sources such as Sigma, ICN Biochemicals, Boehringer Mannheim, etc. Collagenase that is commercially available generally contains a small amount of elastase and/or other enzymes as impurities. Such Impurities are actually beneficial in producing the compositions described herein, since they produce additional cleavages of the collagen molecule that may enhance the yield of 1H11 epitopes contained therein. Such preparations are believed to cleave the collagen molecules at several locations around the pyridinoline cross-links in the N-terminal end of type I collagen.

In a typical procedure for producing these compositions, before contacting the powdered bone with collagenase, it should first be decalcified by standard procedures, washed, heated, cooled to around 37° C. in a water bath, and then contacted with bacterial collagenase. The amount of collagenase will typically be about 1:25–1:100 by weight based on the dry weight of decalcified bone. Digestion is allowed to proceed for at least about 24 hours up to four days or more at room temperature to 40° C. Preferably, the contacting period will be 24 hours to 48 hours at about 37° C. After digestion Is complete, the digest is then purified to remove small peptides (preferably tripeptides), which have a molecular weight of less than about 1000 daltons. For example, purification could be achieved by gel filtration. The composition is next enriched in 1H11 epitopes, as described above, by further purification.

A particular procedure for preparing a collagenase-generated cross-linked peptide composition of the present invention is described as follows:

Preparation of Bacterial Collagenase Generated Cross-linked Peptides

Human cortical bone (femur) was powdered in a Spex mill (SPEX Industries) cooled by liquid $N_2$. Powdered bone was decalcified in 0.5M EDTA, pH 7.5, for 5–10 days at 4° C. The washed collagenous matrix was suspended in 0.1M $CaCl_2$, 0.05M Tris-HCl, pH 7.5, heated at 70° C. for 15 min, cooled to 37° C. in a water bath and bacterial collagenase was added (1:50 per dry weight of decalcified bone). Digestion was continued for a minimum of 24 hours at 37° C. The digest was centrifuged and the supernatant (adjusted to 1% v/v TFA) was passed through a C18-Sep-Pak cartridge (Waters). After washing with 5% (v/v) acetonitrile to remove small collagenous peptides, the enriched cross-linked peptide fragments were eluted with 20% acetonitrile and dried. Further purification could be effected by molecular sieve chromatography (Bio-Gel P10 in 10% (v/v) acetic acid), ion-exchange HPLC (DEAE-5-PWBio-Rad) and reverse-phase HPLC.

Alternatively, the cross-linked N-telopeptides of the bone collagen generated by bacterial collagenase could be highly purified directly by adsorption on the MAb 1H11 affinity column using essentially the above procedure.

The compositions described above may be included as aqueous solutions In containers in a kit or may be included coated on a solid substrate for use in an immunoassay, and the like. Such assays may be carried out as described in the prior related cases that have been Incorporated herein by reference above.

Immunological Procedure for Quantitating Peptides

Immunological binding partners capable of specifically binding to peptide fragments derived from bone collagen obtained from a physiological fluid can be prepared by methods well known in the art. The preferred method for isolating these peptide fragments is described above. By immunological binding partners as used herein is meant antibodies and antibody fragments capable of binding to a telopeptide.

Both monoclonal and polyclonal antibodies specifically binding the peptides disclosed herein and their equivalents are prepared by methods known in the art. For example, Campbell, A. M. *Laboratory Techniques in Biochemistry and Molecular Biology*, Vol. 13 (1986). Elsevier, herein incorporated by reference. It is possible to produce antibodies to the above peptides or their equivalents as isolated. However, because the molecular weights of these peptide fragments are generally less than 5,000, it is preferred that the hapten be conjugated to a carrier molecule. Suitable carrier molecules include, but are not limited to, bovine serum albumin, ovalbumin, thyroglobulin, and keyhole limpet hemocyanin (KLH). Preferred carriers are thyroglobulin and KLH.

It is well known in the art that the orientation of the hapten, as it is bound to the carrier protein, is of critical importance to the specificity of the antiserum. Furthermore, not all hapten-protein conjugates are equally successful immunogens. The selection of a protocol for binding the particular hapten to the carrier protein therefore depends on the amino acid sequence of the urinary peptide fragments selected. For example, if the peptide represented by Formula III is selected, a preferred protocol involves coupling this hapten to keyhole limpet hemocyanin (KLH), or other suitable carrier, with glutaraldehyde. An alternative protocol is to couple the peptides to KLH with a carbodiimide. These protocols help to ensure that the preferred epitope, namely Tyr and a 3-hydroxy-pyridinium cross-link, are presented to the primed vertebrate antibody producing cells (e.g., B lymphocytes).

Other peptides, depending on the source, may require different binding protocols. Accordingly, a number of binding agents may be suitably employed. These include, but are not limited to, carbodiimides, glutaraldehyde, mixed anhydrides, as well as both homobifunctional and heterobifunctional reagents (see for example the Pierce 1986–87 catalog, Pierce Chemical Co., Rockford, Ill.). Preferred binding agents include carbodiimides and heterobifunctional reagents such as m-Maleimidobenzyl-N-hydroxysuccinimide ester (MBS).

Methods for binding the hapten to the carrier molecule are known in the art. See for example, Chard, T., *Laboratory Techniques in Biochemistry Molecular Biology*, Vol. 6 (1987) Partz Elsevier, N.Y., herein incorporated by reference.

Either monoclonal or polyclonal antibodies to the hapten-carrier molecule immunogen can be produced. However, it is preferred that monoclonal antibodies (MAb) be prepared. For this reason it is preferred that immunization be carried out in the mouse. Immunization protocols for the mouse usually include an adjuvant. Examples of suitable protocols are described by Chard, T. (1987) victor supra. Spleen cells from the immunized mouse are harvested and homogenized and thereafter fused with cancer cells in the presence of polyethylene glycol to produce a fused cell hybrid which produces monoclonal antibodies specific to peptide fragments derived from collagen. Examples of such peptides are represented by the formulas given above. Suitable cancer cells include myeloma, hepatoma, carcinoma, and sarcoma cells. Detailed descriptions of this procedure, including screening protocols, protocols for growing selected hybrid cells and harvesting monoclonal antibodies produced by the selected hybrid cells are provided in Galfre, G. and Milstein, C., *Meth. Enzymol.*, 73:1 (1981). A preferred preliminary screening protocol involves the use of peptide fragments derived from bone collagen resorption and containing 3-hydroxypyridinium cross-links in a solid phase radioimmunoassay.

The monoclonal antibodies or other immunological binding partners used in connection with the present are preferably specific for a particular type of collagen telopeptide. For example, assays for the type II or type III collagen degradation telopeptides should preferably be able to distinguish between the type I, type II, and type III peptides. However, in some cases, such selectivity will not be necessary, for example, if it is known that a patient is not suffering degradation of one type of collagen but is suspected of suffering degradation from the assayed type of collagen. Because of the differences in amino acid sequences between the type I, type II, and type III families of telopeptides, cross-reactivity should not occur to a significant degree. Indeed, hybridomas can be selected for during the screening of splenocyte fusion clones that produce monoclonal antibodies specific for the cross-linked telopeptide of interest (and lack affinity for those of the other two collagen types). Based on the differences in sequence of the isolated peptide structures, such specificity is entirely feasible. Peptide fragments of the parent types I, II, and III collagens, suitable for such hybridoma screening, can be prepared from human bone, cartilage and other tissues and used to screen clones from mice immunized appropriately with the individual cross-linked peptide antigens isolated from body fluid.

Immunological binding partners, especially monoclonal antibodies, produced by the above procedures, or equivalent procedures, are employed in various immunometric assays to quantitate the concentration of the peptides having 3-hydroxypyridinium cross-links described above. These immunometric assays comprise a monoclonal antibody or antibody fragment coupled to a detectable marker. Examples of suitable detectable markers include but are not limited to: enzymes, coenzymes, enzyme inhibitors, chromophores, fluorophores, chemiluminescent materials, paramagnetic metals, spin labels, and radionuclides. Examples of standard immunometric methods suitable for quantitating the telopeptides include, but are not limited to, enzyme linked immunosorbent assay (ELISA) (Ingvall, E., *Meth. Enzymol.*, 70 (1981)), radio-immunoassay (RIA), and "sandwich" immunoradiometric assay (IRMA).

In its simplest form, these immunometric methods can be used to determine the absolute rate of bone resorption or collagen degradation by simply contacting a body fluid with the immunological binding partner specific to a collagen telopeptide having a 3-hydroxypyridinium cross-link.

It is preferred that the immunometric assays described above be conducted directly on untreated body fluids (e.g. Urine, blood, serum, or synovial fluid). Occasionally, however, contaminating substances may interfere with the assay necessitating partial purification of the body fluid. Partial purification procedures include, but are not limited to, cartridge adsorption and elution, molecular sieve chromatography, dialysis, ion exchange, alumina chromatography, hydroxyapatite chromatography and combinations thereof.

Test kits, suitable for use in accordance with the present invention, contain monoclonal antibodies prepared as described above that specifically bind to peptide fragments having 3-hydroxypyridinium cross-links derived from collagen degradation found in a body fluid. It is preferred that the monoclonal antibodies of this test kit be coupled to a detectable marker of the type described above. Test kits containing a panel of two or more immunological binding partners are also contemplated. Each immunological binding partner in such a test kit will preferably not cross-react substantially with another type of telopeptide. For example, an immunological binding partner that binds specifically with a type II collagen telopeptide should preferably not cross-react with either a type I or type III collagen telopeptide. A small degree (e.g. 5–10%) of cross-reactivity may be tolerable.

While the invention has been described in conjunction with preferred embodiments, one of ordinary skill after reading the foregoing specification will be able to effect various changes, substitutions of equivalents, and alterations to the subject matter set forth herein. Hence, the invention can be practiced in ways other than those specifically described herein. It is therefore intended that the protection granted by Letters Patent hereon be limited only by the appended claims and equivalents thereof.

The embodiments of the invention in which an exclusive property or privilege is claimed are defined as follows:

1. A composition comprising peptides produced by digesting bone collagen with a protease capable of generating peptides that bind to the monoclonal antibody 1H11, and then purifying the digested bone collagen to increase the concentration of peptides that contain a 3-hydroxypyridinium cross-link by at least 10-fold.

2. A composition according to claim 1, wherein the protease is bacterial collagenase.

3. A method of preparing an immunological binding partner, comprising the steps of immunizing an animal with the purified digested bone collagen composition of claim 1, and harvesting antibodies that bind to peptide fragments derived from bone collagen resorption and containing 3-hydroxypyridinium cross-links.

4. In a method of analyzing a body fluid sample for the presence or concentration of an analyte indicative of a physiological condition, comprising the steps of contacting the body fluid sample with an immunological binding partner which binds to the analyte, detecting binding of the immunological binding partner in the body fluid sample, and correlating any detected binding to the physiological condition, the improvement comprising contacting the body fluid sample with an immunological binding partner produced by immunizing an animal with the purified digested bone collagen of claim 1, and correlating any detected binding to degradation of type I collagen in vivo.

* * * * *

UNITED STATES PATENT AND TRADEMARK OFFICE
CERTIFICATE OF CORRECTION

PATENT NO. : 5,912,131
DATED : June 15, 1999
INVENTOR(S) : D.R. Eyre

It is certified that error appears in the above-identified patent and that said Letters Patent is hereby corrected as shown below:

| COLUMN | LINE | |
|---|---|---|
| [54]<br>Pg. 1, col. 1 | Title | "TYPE 1" should read --TYPE I-- |
| [56]<br>Pg. 1, col. 1 | Refs. Cited<br>(U.S. Pats.) | Please insert the following reference:<br>--07/432,044   11/1989   Termine-- |
| [56]<br>Pg. 1, col. 1 | Refs. Cited<br>(Foreign Pats.,<br>item 4) | "0 4234 428 B1" should read --0 424 428 B1-- |
| [56]<br>Pg. 1, col. 1 | Refs. Cited<br>(Foreign Pats.,<br>item 7) | "2205643" should read --2205643 A-- |
| [56]<br>Pg. 2, col. 1 | Refs. Cited<br>(Other Publs.,<br>item 29) | "Reversed- Phase" should read --Reversed-Phase-- |
| [56]<br>Pg. 2, col. 2 | Refs. Cited<br>(Other Publs.,<br>item 43) | "Society of" should read --Society for-- |
| [56]<br>Pg. 3, col. 2 | Refs. Cited<br>(Other Publs.,<br>item 70) | "Duncan, a." should read --Duncan, A.-- |

UNITED STATES PATENT AND TRADEMARK OFFICE
CERTIFICATE OF CORRECTION

PATENT NO. : 5,912,131
DATED : June 15, 1999
INVENTOR(S) : D.R. Eyre

Page 2 of 5

It is certified that error appears in the above-identified patent and that said Letters Patent is hereby corrected as shown below:

| COLUMN | LINE | |
|---|---|---|
| [56] Pg. 3, col. 2 | Refs. Cited (Other Publs., item 78) | "of type-I" should read --of a type-I-- |
| [56] Pg. 4, col. 1 | Refs. Cited (Other Publs., item 95) | "Rauterbrg," should read --Rauterberg,-- |
| Pg. 1, col. 2 | Attorney, Agent, or Firm | "Christenson" should read --Christensen-- |
| 1 | 1 | "TYPE 1" should read --TYPE I-- |
| 1 | 5 | After "Nov. 22, 1995" insert --,-- |
| 1 | 6 | "contuation" should read --continuation-- |
| 1 | 6 | After "Apr. 19, 1994" insert --,-- |
| 1 | 10 | After "Nov. 21, 1990" insert --,-- |
| 1 | 53 | "Vol. 11" should read --Vol. II-- |
| 2 | 4 | "In the" should read --in the-- |
| 2 | 35 | "type It" should read --type II-- |

UNITED STATES PATENT AND TRADEMARK OFFICE
CERTIFICATE OF CORRECTION

PATENT NO. : 5,912,131
DATED : June 15, 1999
INVENTOR(S) : D.R. Eyre

It is certified that error appears in the above-identified patent and that said Letters Patent is hereby corrected as shown below:

| COLUMN | LINE | |
|---|---|---|
| 3 | 53 | "In body" should read --in body-- |
| 3 | 54 | "In order" should read --in order-- |
| 3 | 56 | "Inventor notes" should read --inventor notes-- |
| 3 | 64-65 | "-dimethyl-amino-benzaldehyde." should read --p-dimethyl-amino-benzaldehyde.-- |
| 4 | 2 | "Index." should read --index.-- |
| 5 | 16 | Before "1981))." insert --(-- |
| 6 | 22 | "Robins'urinary" should read --Robins' urinary-- |
| 8 | 48 | After "glutamine" insert --,-- |
| 8 | 58 | "In the" should read --in the-- |
| 9 | 18 | "Immunological" should read --immunological-- |
| 9 | 64 | "a1 (I)" should read --$\alpha$1(I)-- |
| 10 | 4 | "cross-links." should read --cross-link.-- |

UNITED STATES PATENT AND TRADEMARK OFFICE
CERTIFICATE OF CORRECTION

PATENT NO. : 5,912,131
DATED : June 15, 1999
INVENTOR(S) : D.R. Eyre

Page 4 of 5

It is certified that error appears in the above-identified patent and that said Letters Patent is hereby corrected as shown below:

| COLUMN | LINE | |
|---|---|---|
| 10 | 24-34 | The paragraph beginning with "Amino acid compositions . . ." and ending with " . . . carboxylic acid." should have normal margins. |
| 10 | 53 | "1H11affinity" should read --1H11 affinity-- |
| 11 | 13 | "In the" should read --in the-- |
| 11 | 17 | "In solution" should read --in solution-- |
| 11 | 35 | "protease generated" should read --protease-generated-- |
| 11 | 40 | "protease generated" should read --protease-generated-- |
| 11 | 44 | "protease generated" should read --protease-generated-- |
| 12 | 11 | After "Digestion,"" delete "," |
| 12 | 21 | "Impurities are" should read --impurities are-- |
| 12 | 38 | "Is complete," should read --is complete,-- |

UNITED STATES PATENT AND TRADEMARK OFFICE
CERTIFICATE OF CORRECTION

PATENT NO. : 5,912,131
DATED : June 15, 1999
INVENTOR(S) : D.R. Eyre

It is certified that error appears in the above-identified patent and that said Letters Patent is hereby corrected as shown below:

| COLUMN | LINE | |
|--------|------|---|
| 13 | 4 | "In containers" should read --in containers-- |
| 13 | 7 | "Incorporated" should read --incorporated-- |
| 14 | 2 | "victor" should read --vida-- |
| 14 | 67 | "Urine," should read --urine,-- |
| 15 | 22 | "tide.A" should read --tide. A-- |

Signed and Sealed this

Eighteenth Day of January, 2000

Attest:

Q. TODD DICKINSON

*Attesting Officer*     *Commissioner of Patents and Trademarks*